United States Patent
Kobayashi

(10) Patent No.: US 11,199,637 B2
(45) Date of Patent: Dec. 14, 2021

(54) RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

(71) Applicant: CANON KABUSHIKI KAISHA, Tokyo (JP)

(72) Inventor: Shigeo Kobayashi, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 225 days.

(21) Appl. No.: 16/689,192

(22) Filed: Nov. 20, 2019

(65) Prior Publication Data

US 2020/0166656 A1    May 28, 2020

(30) Foreign Application Priority Data

Nov. 27, 2018  (JP) .............................. JP2018-221679

(51) Int. Cl.
| | |
|---|---|
| *A61B 6/00* | (2006.01) |
| *H04N 5/367* | (2011.01) |
| *G01T 1/208* | (2006.01) |
| *G01N 23/04* | (2018.01) |

(52) U.S. Cl.
CPC .............. *G01T 1/208* (2013.01); *A61B 6/40* (2013.01); *A61B 6/4266* (2013.01); *H04N 5/367* (2013.01); *G01N 23/04* (2013.01); *G01N 2223/42* (2013.01); *G01N 2223/505* (2013.01)

(58) Field of Classification Search
None
See application file for complete search history.

(56) References Cited

U.S. PATENT DOCUMENTS

| | | | | |
|---|---|---|---|---|
| 2005/0286797 | A1* | 12/2005 | Hayaishi | H04N 9/04557 382/274 |
| 2011/0235940 | A1 | 9/2011 | Pavkovich | |
| 2012/0020541 | A1* | 1/2012 | Hayashida | A61B 6/583 382/132 |
| 2018/0234650 | A1* | 8/2018 | Maruyama | H04N 5/142 |
| 2019/0222782 | A1 | 7/2019 | Kobayashi | |
| 2019/0296062 | A1* | 9/2019 | Terauchi | H04N 5/23229 |

* cited by examiner

*Primary Examiner* — Hoon K Song
(74) *Attorney, Agent, or Firm* — Venable LLP

(57) ABSTRACT

A radiation imaging apparatus is provided. The apparatus comprises an image capturing unit that is provided with pixels for converting incident radiation into electrical signals and is configured to output first image data, a storage unit configured to store position information of a first pixel which continuously outputs an abnormal pixel value, a replacing unit configured to generate second image data from the first image data by replacing a pixel value of the first pixel with a preset setting value based on the position information and a correction unit configured to detect a second pixel which is not stored in the storage unit and outputs an abnormal pixel value, and correct the pixel value of the second pixel. The correction unit detects and corrects the second pixel based on the second image data that includes the first pixel whose pixel value has been replaced.

18 Claims, 6 Drawing Sheets

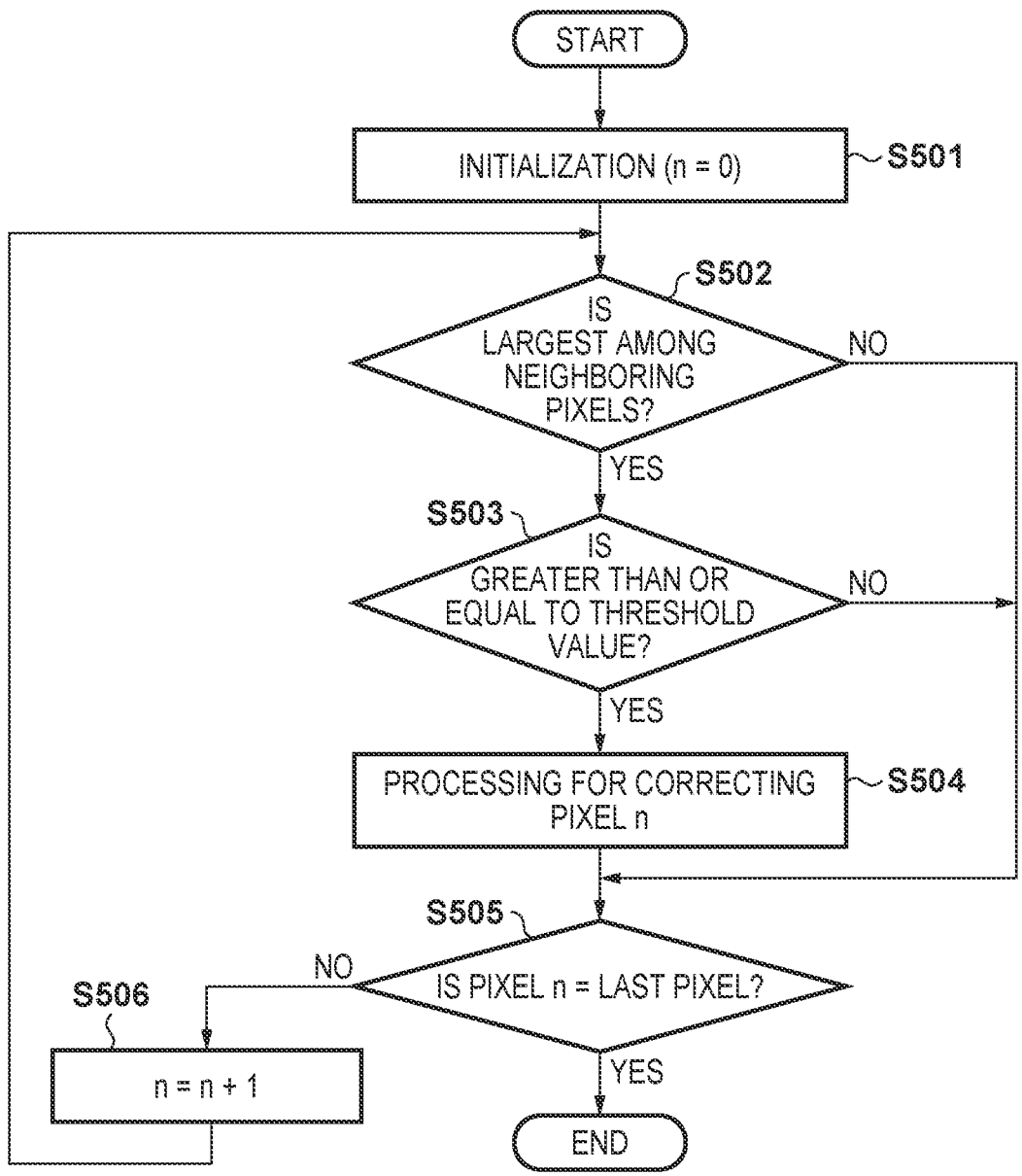

RADIATION IMAGING APPARATUS, RADIATION IMAGING SYSTEM, CONTROL METHOD OF RADIATION IMAGING APPARATUS, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a method of controlling a radiation imaging apparatus, and a non-transitory computer-readable storage medium.

Description of the Related Art

As an imaging apparatus used for medical imaging diagnosis by radiation and non-destructive examination, a radiation imaging apparatus using a Flat Panel Detector (FPD) formed of a semiconductor material has been known. Such a radiation imaging apparatus is used as a digital imaging apparatus for a still image, a moving image, or the like in medical imaging diagnosis, for example.

Among a plurality of pixels arranged in the FPD, there may be a pixel (defective pixel) that continuously outputs an abnormal signal due to a problem in a step for manufacturing the FPD or the like. In addition, there may be a pixel (abnormal pixel) that temporarily outputs an abnormal signal due to the mixing of occasional noise or the like during imaging. In the specification of US-2011-0235940, correction of defective pixels after detection and correction of abnormal pixels is described. In the detection of an abnormal pixel in the specification of US-2011-0235940, it is determined whether or not a pixel of interest is an abnormal pixel by comparing the pixel of interest with a pixel arranged in the neighborhood of the pixel of interest (a neighboring pixel). At this time, by referring to a map (defective pixel map) in which the position information of defective pixels is stored, when there is a defective pixel among the neighboring pixels, an abnormal pixel is detected by comparing pixels other than the defective pixel from among the neighboring pixels with the pixel of interest. When an abnormal pixel is detected, the pixel value of the abnormal pixel is corrected using the pixel values of the pixels other than the defective pixel from the neighboring pixels.

SUMMARY OF THE INVENTION

In the method illustrated in the specification of US-2011-0235940, since a defective pixel map is referred to for each pixel and an abnormal pixel is detected and corrected using pixels other than defective pixels, this can cause degradation of the processing efficiency in detecting and correcting an abnormal pixel.

Some embodiments of the present invention provide techniques that are advantageous for correcting abnormal pixels.

According to some embodiments, a radiation imaging apparatus, comprising: an image capturing unit that is provided with a plurality of pixels for converting incident radiation into electrical signals and is configured to output first image data; a storage unit configured to store position information of, from among the plurality of pixels, a first pixel which continuously outputs an abnormal pixel value; a replacing unit configured to generate second image data from the first image data by replacing a pixel value of the first pixel with a preset setting value based on the position information; and a correction unit configured to detect, from among the plurality of pixels, a second pixel which is not stored in the storage unit and outputs an abnormal pixel value, and correct the pixel value of the second pixel, wherein the correction unit detects and corrects the second pixel based on data that includes the first pixel whose pixel value has been replaced in the second image data, is provided.

According to some other embodiments, a method of controlling a radiation imaging apparatus, wherein the radiation imaging apparatus comprises: an image capturing unit including a plurality of pixels configured to convert incident radiation into electrical signals, a storage unit configured to store position information of, from among the plurality of pixels, a first pixel which continuously outputs an abnormal pixel value; a replacing unit configured to replace the pixel value of the first pixel with a preset setting value based on the position information; a correction unit configured to detect, from among the plurality of pixels, a second pixel which is not stored in the storage unit and outputs an abnormal pixel value, and correct the pixel value of the second pixel, the method comprises: generating second image data by performing processing in accordance with the replacing unit on the first image data output from the image capturing unit; and detecting and correcting the second pixel in accordance with the correction unit, based on, from out of the second image data, data including the first pixel whose pixel value has been replaced, is provided.

According to still other embodiments, a non-transitory computer-readable storage medium storing a program for causing a computer to execute the method of controlling a radiation imaging apparatus, wherein the radiation imaging apparatus comprises: an image capturing unit including a plurality of pixels configured to convert incident radiation into electrical signals, a storage unit configured to store position information of, from among the plurality of pixels, a first pixel which continuously outputs an abnormal pixel value; a replacing unit configured to replace the pixel value of the first pixel with a preset setting value based on the position information; a correction unit configured to detect, from among the plurality of pixels, a second pixel which is not stored in the storage unit and outputs an abnormal pixel value, and correct the pixel value of the second pixel, the method comprises: generating second image data by performing processing in accordance with the replacing unit on the first image data output from the image capturing unit; and detecting and correcting the second pixel in accordance with the correction unit, based on, from out of the second image data, data including the first pixel whose pixel value has been replaced, is provided.

Further features of the present invention will become apparent from the following description of exemplary embodiments (with reference to the attached drawings).

BRIEF DESCRIPTION OF THE DRAWINGS

FIG. 5 is a flow chart illustrating operation of processing for correcting an abnormal pixel of the radiation imaging apparatus of FIG. 1.

DESCRIPTION OF THE EMBODIMENTS

Figure 1:
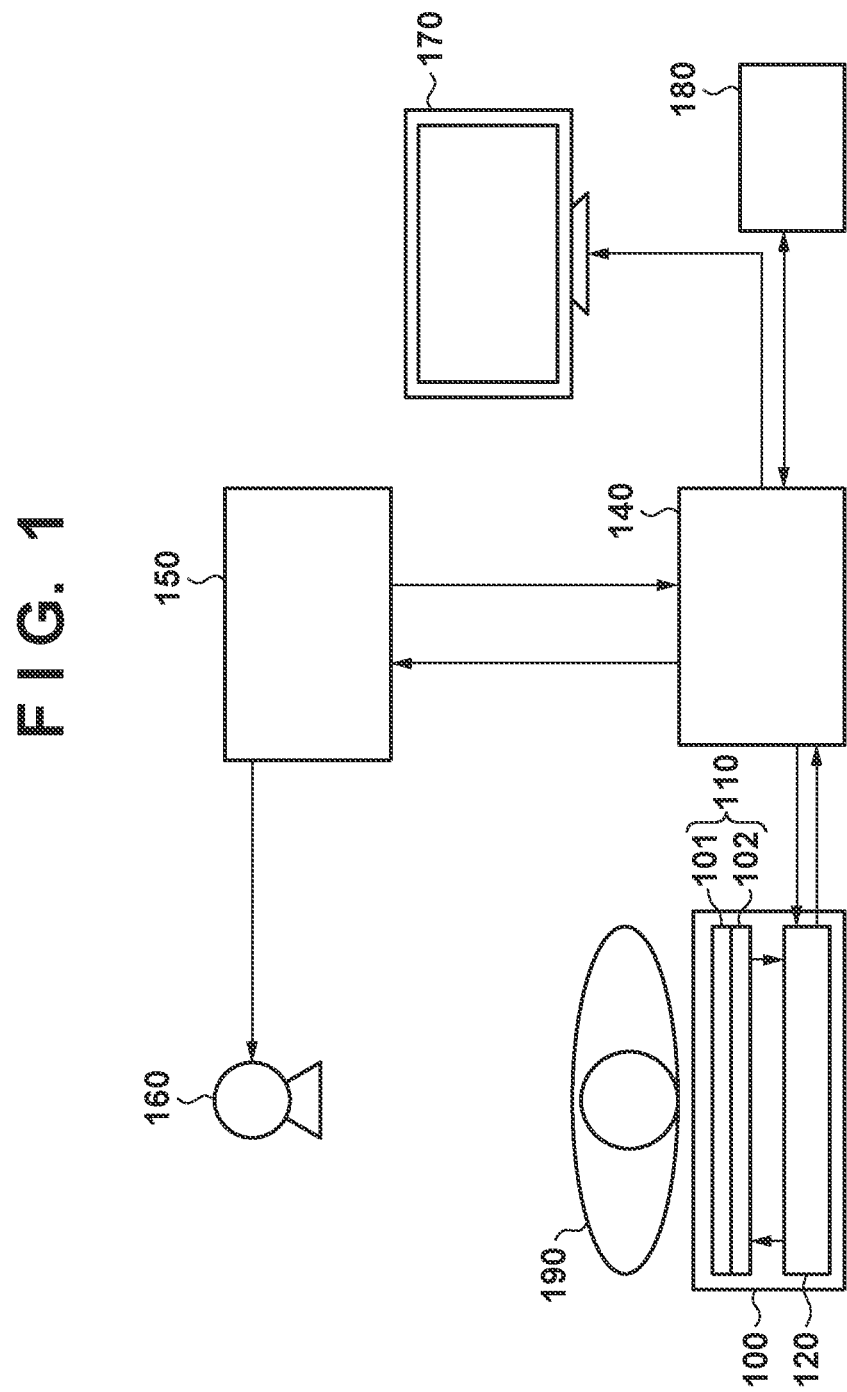
FIG. 1 is a diagram illustrating a configuration example of a radiation imaging system that uses a radiation imaging apparatus according to an embodiment of the present invention.

Hereinafter, specific embodiments of a radiation imaging apparatus according to the present invention will be described with reference to the accompanying drawings. In the following description and the drawings, the same reference numerals denote the same components throughout the plurality of drawings. Therefore, a common configuration will be described with reference to the plurality of drawings, and a description of a configuration to which a common symbol is assigned will be omitted as appropriate. In addition, the radiation in the present invention may include α-rays, β-rays, γ-rays, and the like, which are beams created by particles (including photons) emitted by radioactive decay, and also beams having the same or higher energy, for example, X-rays, particle beams, cosmic rays, and the like.

Referring to FIGS. 1 to 7, a configuration and operation of the radiation imaging apparatus according to an embodiment of the present invention will be described. FIG. 1 is a diagram illustrating a configuration example of a radiation imaging system that uses a radiation imaging apparatus 100 according to an embodiment of the present invention. The radiation imaging system SYS includes a radiation imaging apparatus 100, a control computer 140, a radiation source control unit 150, and a radiation source 160.

The radiation source 160 generates radiation in accordance with a control signal outputted from the radiation source control unit 150, and irradiates the radiation toward the radiation imaging apparatus 100. Radiation irradiated from the radiation source 160 enters the radiation imaging apparatus 100 via a subject 190. The radiation imaging apparatus 100 generates an image corresponding to an irradiated radiation dose, and transmits the image to the control computer 140.

The control computer 140 controls the operation of the entire radiation imaging system SYS. For example, the control computer 140 instructs the radiation source control unit 150 to start or stop irradiation of radiation, and notifies the radiation imaging apparatus 100 of the start or stop irradiation of radiation, thereby synchronizing the radiation source control unit 150 and the radiation imaging apparatus 100. The control computer 140 may be used by a user (a doctor, a radiologist, or the like) to change the settings of the radiation imaging apparatus 100. The control computer 140 may have a built-in display or keyboard for a user to confirm conditions of radiation generated by the radiation source 160, a setting of the radiation imaging apparatus 100, and the like, and to input imaging conditions in the radiation imaging system SYS. As illustrated in FIG. 1, a display unit 170 for a user to confirm a captured radiation image, an imaging condition, and a setting of the radiation imaging system SYS, and a control console 180 for a user to input an imaging condition and settings may be provided separately from the control computer 140.

The radiation imaging apparatus 100 includes an image capturing unit 110 and a control unit 120. The image capturing unit 110 includes a scintillator 101, and an image capturing panel 102 in which a plurality of pixels each including a photoelectric conversion unit for converting light into which the radiation is converted by the scintillator 101 into an electrical signal are arranged. In the present embodiment, the image capturing unit 110 includes the scintillator 101 and the image capturing panel 102, but there is no limitation to this. Configuration may be taken such that the image capturing unit 110 is configured by an image capturing panel in which a plurality of pixels each including a conversion element for directly converting incident radiation into an electrical signal are arranged, without arranging the scintillator 101. The image capturing unit 110 may include a plurality of pixels for converting incident radiation into an electrical signal corresponding to an incident radiation dose.

The control unit 120 controls the entire radiation imaging apparatus 100. The control unit 120 may include a regulator function that receives power from an external power source, a built-in battery, or the like and supplies power to the entire radiation imaging apparatus 100. In addition, the control unit 120 drives the image capturing panel 102, and reads out image data from the image capturing panel 102. Further, the control unit 120 performs correction processing for correcting for characteristics inherent to the image capturing panel 102, on the image data read from the image capturing panel 102. The correction processing performed by the control unit 120 may be correction of an offset or correction of a gain. In addition, although details will be described later, the correction processing executed by the control unit 120 may be interpolation for pixels that continuously output abnormal signals, and correction for pixels that temporarily output abnormal signals due to the mixture of occasional noise or the like during imaging. These correction functions may be provided in the control computer 140. In this case, the correction functions of the control computer 140 and the radiation imaging apparatus 100 can be collectively referred to as a "radiation imaging apparatus" of the present invention.

Figure 2:
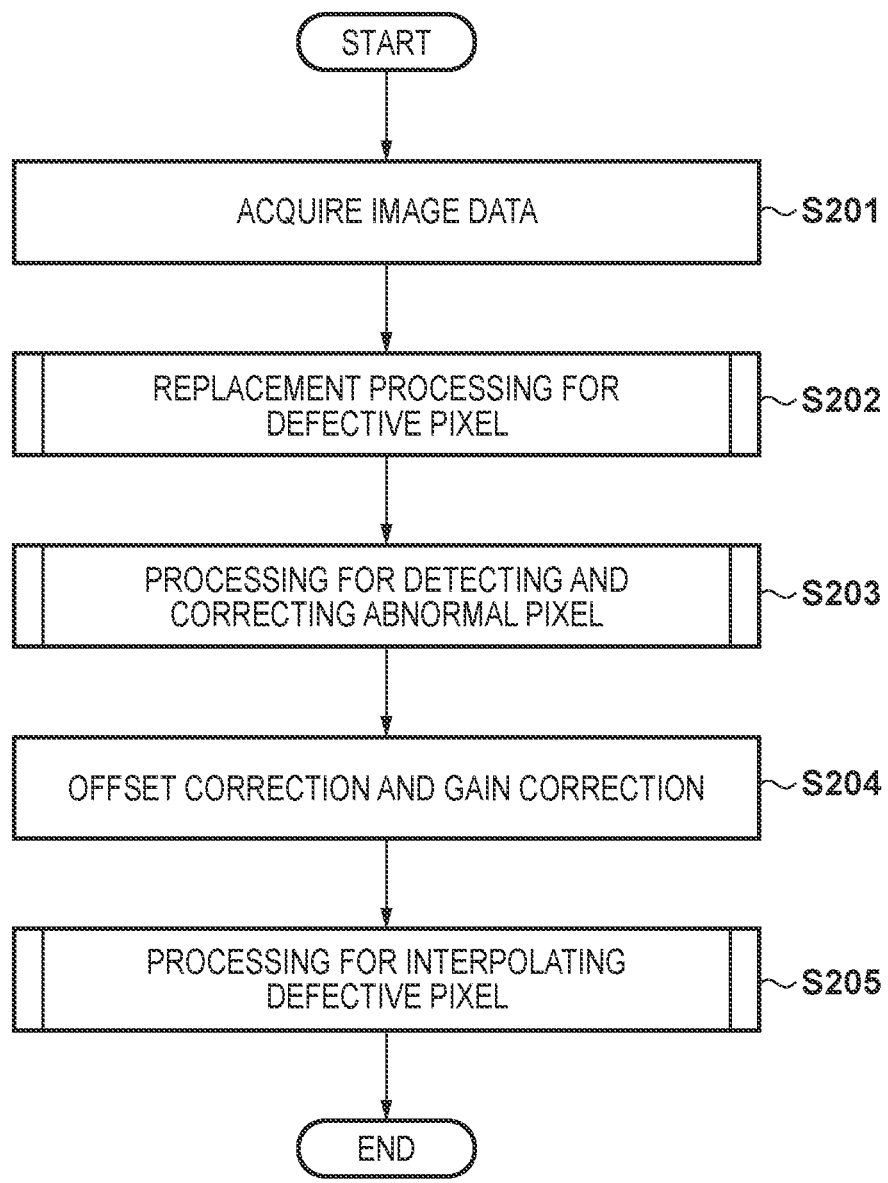
FIG. 2 is a flow chart illustrating steps of correction processing of the radiation imaging apparatus of FIG. 1.

Next, the flow of the correction process performed by the control unit 120 in the present embodiment will be described with reference to FIGS. 2 and 3. FIG. 2 is a flowchart illustrating steps of correction processing of image data of the radiation imaging apparatus 100.

After capturing a radiation image using the radiation imaging system SYS, first, in step S201, the control unit 120 acquires image data (first image data) outputted from the image capturing panel 102 of the image capturing unit 110. In step S202, the acquired image data is subjected to a replacement process that replaces a signal value of a pixel that constantly outputs an abnormal signal (a first pixel: hereinafter, may be referred to as a defective pixel) with a preset setting value. Next, in step S203, the control unit 120 detects a pixel (a second pixel: hereinafter may be referred to as an abnormal pixel) that temporarily outputs an abnormal signal due to occasional noise or the like, in the image data that has been outputted from the image capturing unit 110 and subjected to the replacement process. Further, the control unit 120 corrects the pixel value of the detected abnormal pixel. After processing for correcting the abnormal pixel is performed, in step S204, the control unit 120 performs the respective processes of the offset correction and the gain correction according to a dark image, an imaging condition, and the like. After performing the offset correction and the gain correction, in step S205, the control unit 120 performs an interpolating process on the defective pixel.

Figure 3:
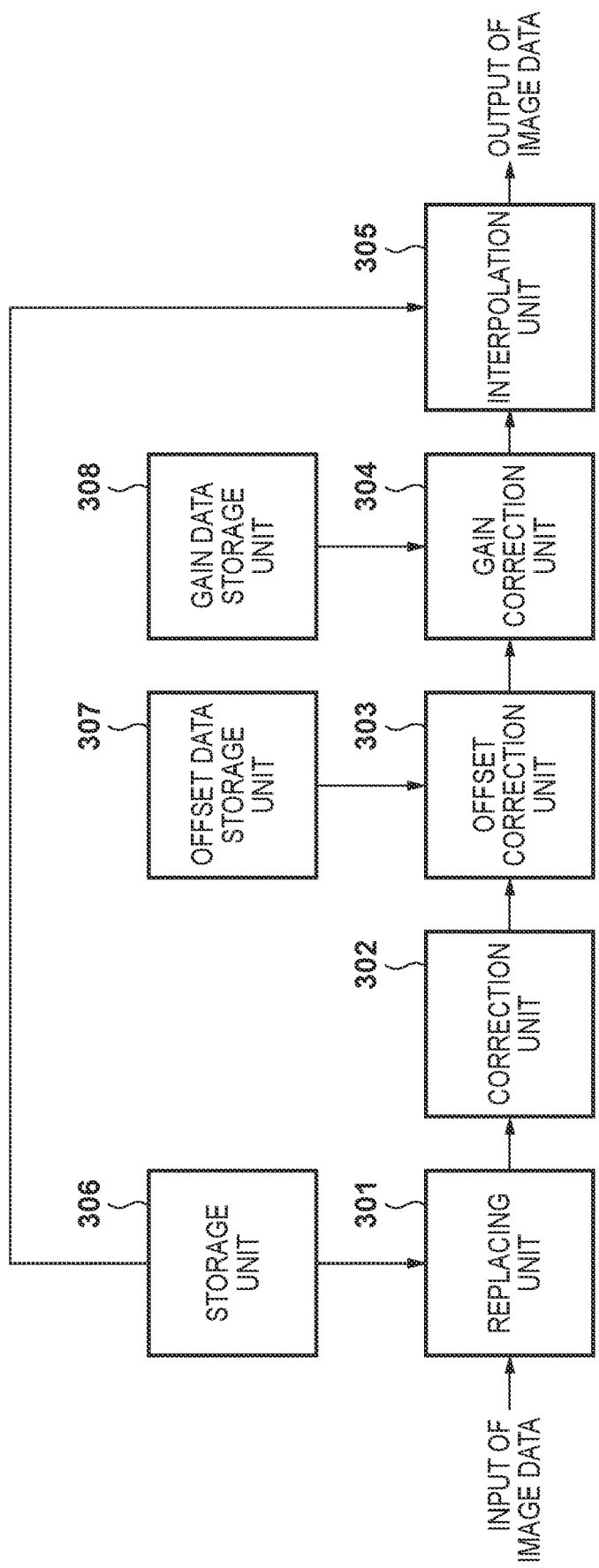
FIG. 3 is a block diagram illustrating a method of correction processing of the radiation imaging apparatus of FIG. 1.

FIG. 3 is a block diagram illustrating steps of processing for correcting image data of the radiation imaging apparatus 100. In order to perform correction processing of image data output from the image capturing unit 110, the control unit 120 includes a replacing unit 301, a correction unit 302, an offset correction unit 303, a gain correction unit 304, and an interpolation unit 305. The control unit 120 also includes a storage unit 306 that stores position information of defective pixels that constantly output abnormal pixel values from among the plurality of pixels. Although the storage unit 306 is described as being included in the control unit 120, the storage unit 306 may be arranged independently of the control unit 120. The position information of a defective pixel is acquired by, for example, inspection before shipment of the radiation imaging apparatus 100, calibration work after shipment, or the like, and is stored in the storage unit 306 in advance.

With respect to the image data output from the image capturing unit 110, first, the replacing unit 301 performs replacement processing for replacing the pixel value of a defective pixel with a preset setting value using the defective pixel position information stored in the storage unit 306. Here, a defective pixel that continuously outputs an abnormal signal is a pixel that continuously outputs an abnormal signal due to, for example, a problem in a manufacturing step of the image capturing panel 102 or change over time. Therefore, as described above, it is a pixel whose position information can be stored in the storage unit 306 in advance. The defective pixel may be, for example, a pixel that continuously outputs a pixel value of the same value regardless of the dose of incident radiation. By this replacement processing, image data (second image data) in which the pixel value of a defective pixel is replaced with a preset setting value is generated.

Next, with respect to the image data processed by the replacing unit, the correction unit 302 detects, from among the plurality of pixels, an abnormal pixel value which is not stored in the storage unit 306 and which outputs an abnormal pixel value, and corrects the pixel value of the abnormal pixel. Here, an abnormal pixel which temporarily outputs an abnormal signal is a pixel whose pixel value indicates an abnormal value at random in both spatial and temporal terms due to the mixture of occasional noise or the like during imaging. For example, this may occur in a case such as when an impact is applied to the radiation imaging apparatus 100 during imaging. In a configuration using the scintillator 101 as in the image capturing unit 110 of the present embodiment, radiation photons that have not been absorbed by the scintillator 101 and have passed through the scintillator 101 (not converted into light) may be incident on the image capturing panel 102. When a radiation photon causes a photoelectric effect in the photoelectric conversion unit of the pixel of the image capturing panel 102 and is converted into an electrical signal, the pixel may output an abnormally large pixel value as compared with a normal pixel value. An abnormal pixel is generally considered to output a pixel value having a value larger than that of a normal pixel. Since abnormal pixels that appear at random spatially and temporally cannot be registered in the storage unit 306, the correction unit 302 detects pixels that output abnormal pixel values among pixels that are not stored in the storage unit 306, and corrects the pixel values.

In the offset correction unit 303, processing for correcting an offset using offset data stored in the offset data storage unit 307 is performed with respect to the image data processed by the correction unit 302. For the offset data, a signal (dark image) output from each pixel of the image capturing panel 102 in a state where radiation is not irradiated before imaging or the like is acquired and stored in the offset data storage unit 307. Next, in the gain correction unit 304, processing for correcting the gain of the image data processed by the offset correction unit 303 using the gain data that is in accordance with an imaging condition or the like and is stored in the gain data storage unit 206 is performed.

Next, the image data processed by the gain correction unit 304 is subjected to spatial interpolation processing in the interpolation unit 305 based on the position information of a defective pixel registered in the storage unit 306. More specifically, the interpolation unit 305 generates the pixel value of the defective pixel based on the position information of the defective pixel stored in the storage unit 306 and the pixel value of pixels arranged in the neighborhood of the defective pixel among the plurality of pixels arranged in the image capturing panel 102. The interpolation unit 305 sets the generated pixel value as the pixel value of the defective pixel. The image data processed by the interpolation unit 305 is transferred to the control computer 140 as output data.

Next, each step of the correction process illustrated in FIGS. 2 and 3 will be described in detail with reference to FIGS. 4 to 7.

Figure 4:
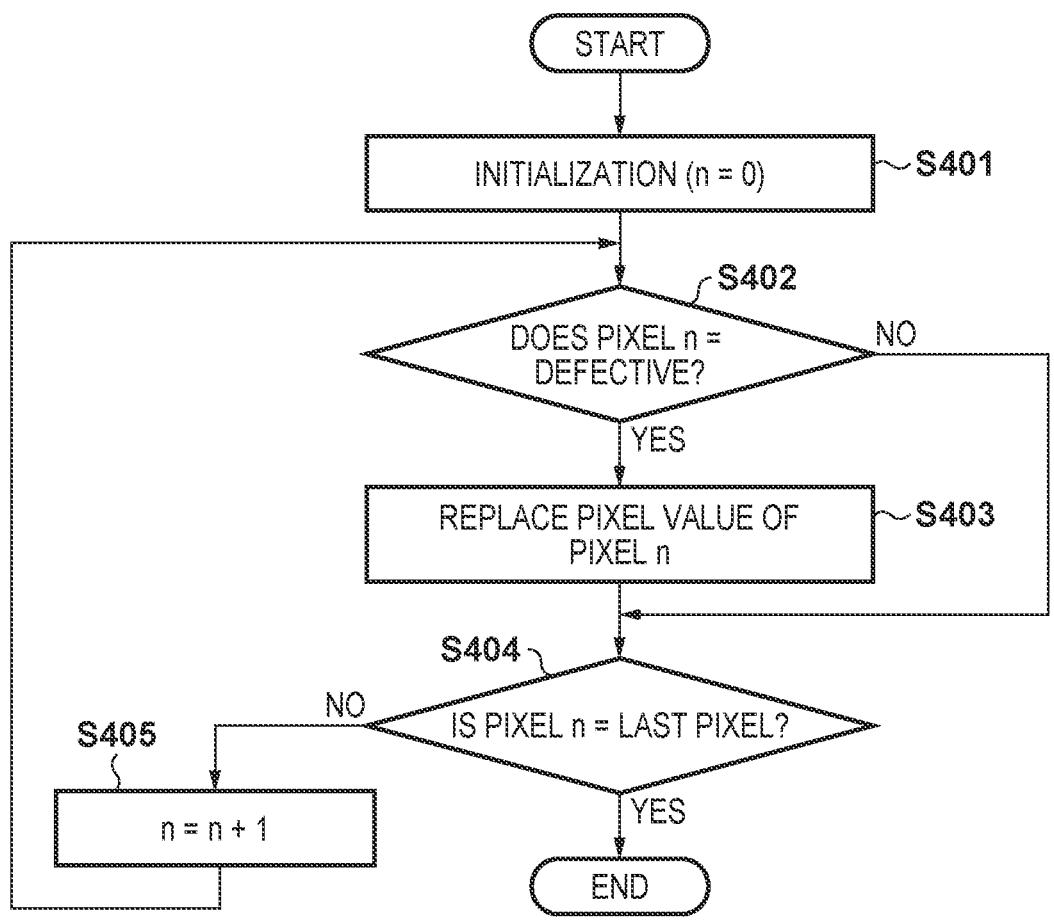
FIG. 4 is a flow chart illustrating operation of processing for replacing a defective pixel of the radiation imaging apparatus of FIG. 1.

FIG. 4 is a flowchart for explaining in detail a replacement process for replacing a pixel value of a defective pixel in step S202 of FIG. 2. This processing corresponds to the processing of the replacing unit 301 in FIG. 3. This replacement process is a process required to suppress the effects of a defective pixel on the pixel value of an abnormal pixel after correction in the correction of the abnormal pixel in step S203. Further, in step S202 in which the abnormal pixel has not been detected, processing for interpolating a defective pixel is not performed. This is because if an abnormal pixel exists in the neighborhood of a defective pixel, because the abnormal pixel is not registered in the storage unit 306, the interpolation unit 305 may perform interpolation of the defective pixel using pixels that include the abnormal pixel.

Figures 6A, 6B, 6C, 6D, 7:
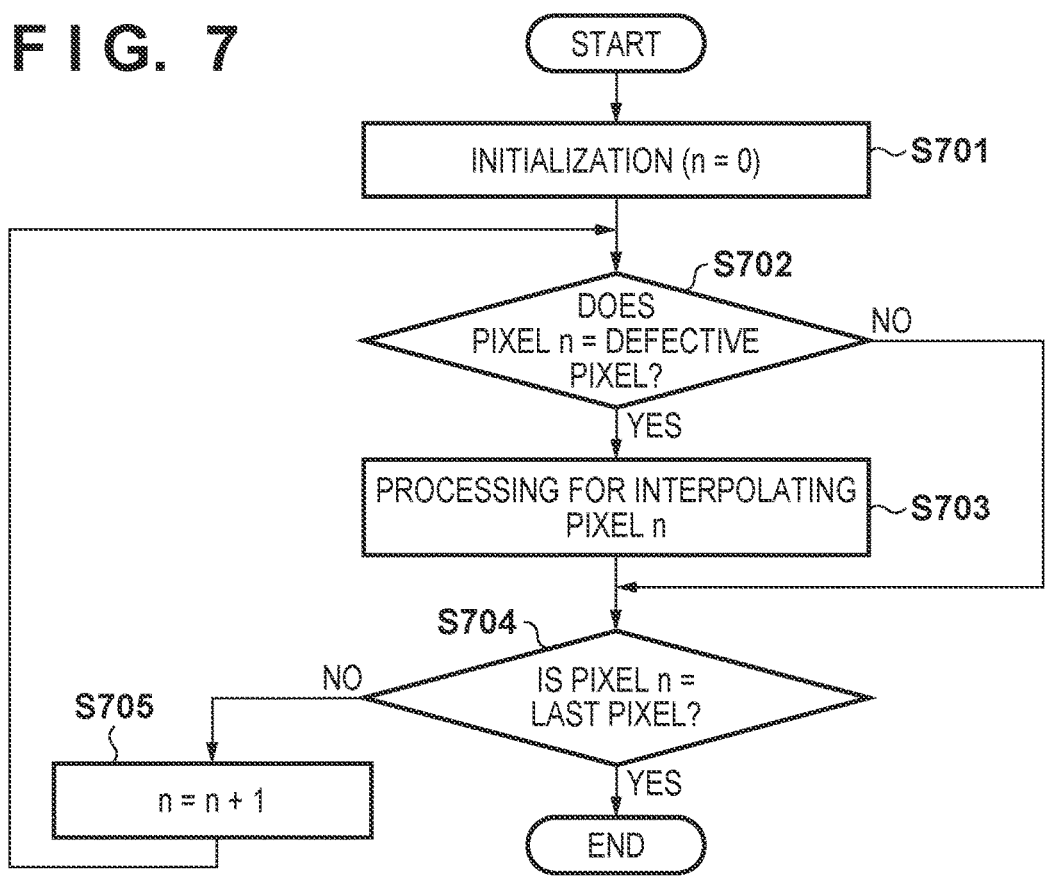
FIGS. 6A to 6D are diagrams illustrating an example of the correction processing of FIG. 5.
FIG. 7 is a flow chart illustrating operation of interpolation processing for a defective pixel of the radiation imaging apparatus of FIG. 1.

In FIGS. 4, 5, and 7, a pixel for which processing is underway is described as "pixel n". "n" is a number corresponding to each pixel. For example, when 1000 pixels are arranged in the image capturing panel 102 of the image capturing unit 110, "n" is the number of pixels numbered from 0 to 999 in order for each pixel.

First, in step S401, the replacing unit 301 initializes the pixel number "n" (n=0) with respect to the image data outputted from the image capturing unit 110. Next, in step S402, the replacing unit 301 determines whether or not the pixel n is a defective pixel based on position information of defective pixels stored in the storage unit 306. If it is determined in step S402 that the pixel n is not a defective pixel, the replacing unit 301 transitions to step S404. If it is determined in step S402 that the pixel n is a defective pixel, the replacing unit 301 transitions to step S403. Upon transitioning to step S403, the replacing unit 301 replaces the pixel value of the pixel n determined to be a defective pixel with a preset setting value. For example, the setting value may be a minimum normal value for pixel values of the plurality of pixels. Here, the minimum normal value means a pixel value of "0" when the pixels are designed to output pixel values of 256 levels from 0 (dark side) to 255, for example. Also, for example, the setting value may be a median value of normal pixel values for the plurality of pixels. Here, a median value of the pixel value of the normal pixel may be, for example, a pixel value of "128" when the pixels are designed as described above, or may be an arbitrary pixel value between "64" and "192" that is set by a user or in accordance with an imaging condition, or the like, for example. Hereinafter, description is given with the replacing unit 301 replacing the pixel value of the defective pixel with the minimum normal pixel value.

Upon transitioning to step S404, the replacing unit 301 determines whether or not the pixel n is the last pixel. If it is determined in step S404 that the pixel n is not the last pixel, the replacing unit 301 transitions to step S405. The replacing unit 301 advances "n" to "n+1" in step S405, and subsequently repeats the process from step S402. If it is determined in step S404 that the pixel n is the last pixel, the steps of the replacement process in the replacing unit 301 end.

Next, referring to FIG. 5 and FIGS. 6A to 6D, description will be given in detail regarding the detection of an abnormal pixel and correction of the pixel value of the abnormal pixel in step S203 of FIG. 2. This processing corresponds to the processing of the correction unit 302 in FIG. 3.

FIG. 5 is a flowchart illustrating the flow of processing for detecting and correcting an abnormal pixel. FIGS. 6A to 6D are diagrams illustrating an example of processing for detecting and correcting an abnormal pixel. FIG. 6A illustrates one pixel arranged in the image capturing panel 102 of the image capturing unit 110, and the N in the pixel indicates an order of a magnitude relation of pixel values in FIGS. 6B to 6D. In FIGS. 6B to 6D, the magnitude relation of the pixel values is sequentially represented with "1" for N of the pixel indicating the smallest pixel value and "9" for N of the pixel indicating the largest pixel value. FIG. 6B illustrates an example in which pixel values are compared with each other among nine pixels including eight neighboring pixels arranged in the neighborhood of the target pixel, with the pixel in the center as a determination target pixel for detecting an abnormal pixel. For comparison in accordance with nine pixels, N has values from 1 for a pixel which outputs the smallest pixel value to 9 for a pixel which outputs the largest pixel value. FIGS. 6C and 6D are diagrams illustrating a correction processing method for correcting the pixel value of an abnormal pixel.

In the present embodiment, the neighboring pixels are the eight pixels surrounding the target pixel as illustrated in FIG. 6B, but there is no limitation to this. For example, the neighboring pixels may be four pixels adjacent to the target pixel (e.g., pixels arranged on to the top, bottom, left, and right of the target pixel). Further, for example, the neighboring pixels may be the 24 pixels included in a 5×5 matrix surrounding the target pixel.

First, processing for detecting an abnormal pixel and correcting the pixel value of the abnormal pixel will be described with reference to the flow chart illustrated in FIG. 5.

First, in step S501, the correction unit 302 initializes the pixel number "n" (n=0) with respect to the image data processed by the replacing unit 301. Next, the correction unit 302 determines whether or not the pixel n is an abnormal pixel. First, in step S502, the correction unit 302 compares the pixel value of the pixel n with the pixel value of neighboring pixels arranged in the neighborhood of the pixel n. FIG. 6B illustrates an example of a determination result in step S502. If it is determined in step S502 that the pixel value of the pixel n is the largest among the pixel values of the pixel n and the neighboring pixels, the correction unit 302 transitions to step S503. If it is determined in step S502 that the pixel value of the pixel n is not the largest among the pixel values of the pixel n and the neighboring pixels, the correction unit 302 determines that the pixel n is not an abnormal pixel, and transitions to step S505.

As illustrated in FIG. 6B, when the pixel n is the largest of the pixel values of the pixel n and the neighboring pixels in step S502, the correction unit 302 determines whether or not the pixel value of the pixel n is greater than or equal to a set threshold value in step S503. When the pixel value of the pixel n is greater than or equal to the threshold value, the correction unit 302 determines that the pixel n is an abnormal pixel and transitions to step S504. As described above, an abnormal pixel is generally considered to output a pixel value having a value larger than that of a normal pixel. A defective pixel is replaced with the pixel having the smallest pixel value in step S202 illustrated in FIG. 2. Therefore, when the pixel value of the pixel n is greater than or equal to the threshold value, the correction unit 302 can determine that the pixel n is an abnormal pixel. When the pixel value of the pixel n is less than the threshold value, the correction unit 302 determines that the pixel n is not an abnormal pixel and transitions to step S505.

By performing step S502 and step S503, the correction unit 302 detects an abnormal pixel based on data that includes a defective pixel whose pixel value has been replaced among the image data in which the pixel value of a defective pixel has been replaced by the replacing unit 301. More specifically, the correction unit 302 detects an abnormal pixel by using, from among the plurality of pixels, pixel values of pixels whose pixel values have not been replaced by the replacing unit 301, and pixel values replaced by the setting value for defective pixels. As a result, from a plurality of pixels arranged in the image capturing panel 102 of the image capturing unit 110, a pixel, which outputs a pixel value greater than or equal to the set threshold value and is not stored in the storage unit 306, is detected as an abnormal pixel.

In this manner, the correction unit 302 detects an abnormal pixel with reference to pixel values replaced with the setting value for defective pixels. In other words, in the detection of an abnormal pixel, the correction unit 302 does not need to refer to the position information of defective pixels that is stored in the storage unit 306 to determine whether or not a defective pixel is included in the neighboring pixels of each pixel that is to be a target for abnormal pixel detection. As a result, the processing efficiency for detecting abnormal pixels can be improved.

In the present embodiment, the correction unit 302 compares the pixel n whose pixel value is determined to be larger than the pixel values of the neighboring pixels in step S502 with the threshold value in step S503, but there is no limitation to this. For example, configuration may be taken such that step S502 is omitted, and the correction unit 302 detects an abnormal pixel by determining whether or not the pixel values of all the pixels n included in the image data are greater than or equal to the threshold value. The threshold value for a case of detecting an abnormal pixel may be set by the user in accordance with, for example, imaging conditions. Further, for example, configuration may be taken such that a threshold value corresponding to an imaging condition or the like is stored in a memory or the like in the control computer 140, and when the user sets the imaging condition, the threshold value is transferred from the control computer 140 to the control unit 120 of the radiation imaging apparatus 100.

When an abnormal pixel is detected, the correction unit 302 performs a correction process on the pixel value of the abnormal pixel in step S504. The correction process performed by the correction unit 302 in step S504 will be described by referring to FIGS. 6C and 6D. Here, description is given for an example in which the center pixel illustrated in FIG. 6B is detected as an abnormal pixel, and the correction unit 302 corrects the pixel value of the abnormal pixel based on the pixel value of neighboring pixel arranged in the neighborhood of the abnormal pixel among the plurality of pixels.

For example, as illustrated in FIG. 6C, the correction unit 302 may change the pixel value of the abnormal pixel to the same pixel value as that of the pixel outputting the largest pixel value among the neighboring pixels. For example, as illustrated in FIG. 6D, the correction unit 302 may change the pixel value of the abnormal pixel to the pixel value of a pixel that outputs a median value among the neighboring pixels. Here, the median value may be a pixel value of a pixel outputting the fourth or fifth pixel value from the lowest of the eight neighboring pixels in the case of the configuration illustrated in FIG. 6D. Further, for example, the average value of the pixel value of the pixel that has output the fourth pixel value and the pixel that has output the fifth pixel value may be used. For example, the correction unit 302 may change the pixel value of the abnormal pixel to the average value of the pixel values output from the neighboring pixels. In such a case, the pixel value of the defective pixel is replaced with the smallest pixel value in step S202 illustrated in FIG. 2. Therefore, the correction unit 302 may change the pixel value of the abnormal pixel to the average value of the pixel values output from pixels other than the pixel outputting the largest pixel value and the pixel outputting the smallest pixel value, among the neighboring pixels. For example, the correction unit 302 may change the pixel value of the abnormal pixel to the same pixel value as that of the pixel outputting the second largest pixel value among the neighboring pixels. By changing the pixel value to the second largest value, even when another abnormal pixel is included in the neighboring pixels, it is possible to suppress further influence of abnormal pixels and improve the accuracy of correction of abnormal pixels.

The correction of an abnormal pixel in step S504 is not limited to spatial correction using pixels arranged in the neighborhood of an abnormal pixel as described above. For example, in the case where image capturing is performed continuously, such as image capturing of a moving image, the correction unit 302 may correct an abnormal pixel using the pixel values of pixels at the same position in frames before and after the frame in which the abnormal pixel occurred. For example, the correction unit 302 may set the pixel value of an abnormal pixel to the same pixel value as a pixel value of the previous frame or the subsequent frame. For example, the correction unit 302 may correct the pixel value of the abnormal pixel based on the pixel value of two or more frames, such as the average value of the pixel values of the previous frame and the pixel values of the subsequent frame.

In addition, the correction unit 302 may be configured to be able to correct the pixel value of an abnormal pixel by using a method selected from at least two types of correction methods as described above. In this case, the correction unit 302 may further include a method setting unit for selecting a processing method for correcting an abnormal pixel. For example, the method setting unit may select the correction method according to a user's designation. In addition, for example, the method setting unit may appropriately select a processing method for correcting an abnormal pixel in accordance with an imaging condition or the like.

By performing step S504, the correction unit 302 corrects an abnormal pixel based on data that includes a defective pixel whose pixel value has been replaced among the image data in which the pixel value of a defective pixel has been replaced by the replacing unit 301. More specifically, the correction unit 302 corrects an abnormal pixel by using, from among the plurality of pixels, pixel values of pixels whose pixel values have not been replaced by the replacing unit 301, and pixel values replaced by the setting value for defective pixels. As described above, when an abnormal pixel is detected from a plurality of pixels, even if a defective pixel is included in neighboring pixels, the correction unit 302 corrects the abnormal pixel by referring to a pixel value replaced with the setting value for defective pixels. In other words, in the correction of an abnormal pixel, the correction unit 302 does not need to refer to the position information of defective pixels that is stored in the storage unit 306 to determine whether or not a defective pixel is included in the neighboring pixels of each detected abnormal pixel. As a result, the processing efficiency for correcting abnormal pixels can be improved.

Upon transitioning to step S505, the correction unit 302 determines whether or not the pixel n is the last pixel. If it is determined in step S505 that the pixel n is not the last pixel, the correction unit 302 transitions to step S506. The correction unit 302 advances "n" to "n+1" in step S506, and subsequently repeats the process from step S502. If it is determined in step S505 that the pixel n is the last pixel, the steps of detecting and correcting abnormal pixels in the correction unit 302 end.

Next, referring to FIG. 7, an interpolation process for interpolating pixel values of defective pixels in step S205 of FIG. 2 will be described in detail. FIG. 7 is a flowchart illustrating a flow of interpolation processing for defective pixels. This processing corresponds to the processing of the interpolation unit 305 in FIG. 3.

The interpolation unit 305 first initializes the pixel number "n" in step S701. Next, in step S702, the interpolation unit 305 determines whether or not the pixel n is a defective pixel based on position information of defective pixels stored in the storage unit 306. If it is determined in step S702 that the pixel n is not a defective pixel, the interpolation unit 305 transitions to step S704. If it is determined in step S702 that the pixel n is a defective pixel, the interpolation unit 305 transitions to step S703. Upon transitioning to step S403, the interpolation unit 305 interpolates the pixel value of the pixel n determined to be a defective pixel based on the pixel values of, among the plurality of pixels, pixels that are arranged in the neighborhood of the pixel n determined to be the defective pixel. For example, the interpolation unit 305 changes it to the average value of the pixel values of the pixels arranged in the neighborhood of the pixel n determined as the defective pixel among the plurality of pixels.

The interpolation unit 305 performs processing on image data for which processing for abnormal pixels has been performed by the correction unit 302. This suppresses the influence of the pixel values of abnormal pixels in the interpolation of a defective pixel. In the present embodiment, as illustrated in FIG. 3, the interpolation unit 305 performs processing on the image data processed by the offset correction unit 303 and the gain correction unit 304, but there is no limitation to this. The interpolation unit 305 may perform interpolation of defective pixels before processing by the offset correction unit 303 and the gain correction unit 304 is performed.

In addition, as a method of correcting a defective pixel, a method of employing an average value of pixel values of pixels arranged in the neighborhood of the pixel n determined to be a defective pixel has been described, but there is no limitation to this. For example, the interpolation unit 305 may complement the pixel value of the pixel n determined to be a defective pixel by using the median value of the pixel values of pixels arranged in the neighborhood of the pixel n determined to be the defective pixel. In addition, for example, the pixel value of the defective pixel is replaced with the smallest pixel value in step S202 illustrated in FIG. 2. Therefore, the interpolation unit 305 may correct the pixel value of the pixel n, which is determined to be the defective pixel from the stored information stored in the storage unit 306, to be the average value of the pixel values output from pixels other than the pixel outputting the smallest pixel value from among neighboring pixels. This makes it possible to maintain the accuracy of interpolation of the pixel value of the pixel n determined to be a defective pixel even when there is another defective pixel in the neighborhood of the pixel n determined to be the defective pixel.

Upon transitioning to step S704, the interpolation unit 305 determines whether or not the pixel n is the last pixel. If it is determined in step S704 that the pixel n is not the last pixel, the interpolation unit 305 transitions to step S705. The interpolation unit 305 advances "n" to "n+1" in step S705, and subsequently repeats the process from step S702. If it is determined in step S704 that the pixel n is the last pixel, the steps for interpolation of a defective pixel in the interpolation unit 305 end.

As described above, in the present embodiment, before the detection of an abnormal pixel is performed, the pixel value of a defective pixel is replaced with a value having little influence on the detection and correction of an abnormal pixel. When detecting an abnormal pixel, this eliminates the need to determine whether or not there is a defective pixel in the neighborhood of each pixel, for each pixel that is a target of detection. In addition, when the pixel value of an abnormal pixel is corrected, it is not necessary to determine whether the correction is performed based on all neighboring pixels or the correction is performed based on the pixels obtained by removing the defective pixel from the neighboring pixels, for each detected abnormal pixel. This makes it possible to suppress a decrease in efficiency for detection and correction of abnormal pixels.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-221679, filed Nov. 27, 2018, which is hereby incorporated by reference herein in its entirety.

What is claimed is:

1. A radiation imaging apparatus, comprising:
   an image capturing unit that is provided with a plurality of pixels for converting incident radiation into electrical signals and is configured to output first image data;
   a storage unit configured to store position information of, from among the plurality of pixels, a first pixel which continuously outputs an abnormal pixel value;
   a replacing unit configured to generate second image data from the first image data by replacing a pixel value of the first pixel with a preset setting value based on the position information; and
   a correction unit configured to detect, from among the plurality of pixels, a second pixel which is not stored in the storage unit and outputs an abnormal pixel value, and correct the pixel value of the second pixel,
   wherein the correction unit detects and corrects the second pixel based on data that includes the first pixel whose pixel value has been replaced in the second image data.

2. The radiation imaging apparatus according to claim 1, wherein the correction unit detects and corrects the second pixel using a pixel value of a pixel, from among the plurality of pixels, whose pixel value is not replaced by the replacing unit, and a pixel value replaced by the setting value of the first pixel.

3. The radiation imaging apparatus according to claim 1, wherein the correction unit refers to a pixel value replaced by the setting value of the first pixel in the detection and correction of the second pixel.

4. The radiation imaging apparatus according to claim 1, wherein the setting value is a minimum value of normal pixel values for the plurality of pixels.

5. The radiation imaging apparatus according to claim 1, wherein the correction unit detects, as the second pixel, a pixel, among the plurality of pixels, that outputs a pixel value greater than or equal to a set threshold value.

6. The radiation imaging apparatus according to claim 1, wherein the correction unit corrects a pixel value of the second pixel based on a pixel value of, from among the plurality of pixels, a neighboring pixel arranged in a neighborhood of the second pixel.

7. The radiation imaging apparatus according to claim 6, wherein the correction unit changes the pixel value of the second pixel to the same pixel value as pixel that outputs a largest pixel value among the neighboring pixels.

8. The radiation imaging apparatus according to claim 6, wherein the correction unit changes the pixel value of the second pixel to the same pixel value as pixel that outputs a median value among the neighboring pixels.

9. The radiation imaging apparatus according to claim 6, wherein
the correction unit,
is configured to be able to correct the pixel value of the second pixel using a method selected from at least two types,
the radiation imaging apparatus further comprises a setting unit configured to select the method,
and the method comprises:
a method of changing the pixel value of the second pixel to the same pixel value as that of a pixel that outputs a largest pixel value of the neighboring pixels, and
a method of changing the pixel value of the second pixel to a pixel value of a pixel that outputs a median value of the neighboring pixels.

10. The radiation imaging apparatus according to claim 9, wherein the setting unit selects the method according to imaging conditions at a time of imaging.

11. The radiation imaging apparatus according to claim 1, further comprising:
an interpolation unit configured to generate a pixel value of the first pixel based on the position information and a pixel value of a pixel, among the plurality of pixels, that is arranged in a neighborhood of the first pixel,
wherein the interpolation unit performs processing on the second image data that has been processed by the correction unit.

12. The radiation imaging apparatus according to claim 11, further comprising:
an offset correction unit configured to correct an offset of the image data; and a gain correction unit configured to correct a gain of the image data,
wherein the offset correction unit and the gain correction unit perform processing on the second image data that has been processed by the correction unit, and
the interpolation unit performs processing on the second image data that has been processed by the correction unit, the offset correction unit, and the gain correction unit.

13. The radiation imaging apparatus according to claim 11, wherein the interpolation unit corrects a pixel value of the first pixel based on a pixel value of, among the plurality of pixels, a pixel arranged in the neighborhood of the first pixel.

14. The radiation imaging apparatus according to claim 13, wherein the interpolation unit changes the pixel value of the first pixel to an average value of pixel values of pixels arranged in a neighborhood of the first pixel, from among the plurality of pixels.

15. The radiation imaging apparatus according to claim 1, wherein
the image capturing unit further includes a scintillator, and
each of the plurality of pixels includes a photoelectric conversion unit for converting light converted from radiation by the scintillator into an electrical signal.

16. A radiation imaging system, comprising:
the radiation imaging apparatus according to claim 1, and
a radiation source configured to irradiate radiation with respect to the radiation imaging apparatus.

17. A method of controlling a radiation imaging apparatus, wherein
the radiation imaging apparatus comprises:
an image capturing unit including a plurality of pixels configured to convert incident radiation into electrical signals,
a storage unit configured to store position information of, from among the plurality of pixels, a first pixel which continuously outputs an abnormal pixel value;
a replacing unit configured to replace the pixel value of the first pixel with a preset setting value based on the position information;
a correction unit configured to detect, from among the plurality of pixels, a second pixel which is not stored in the storage unit and outputs an abnormal pixel value, and correct the pixel value of the second pixel,
the method comprises:
generating second image data by performing processing in accordance with the replacing unit on the first image data output from the image capturing unit; and
detecting and correcting the second pixel in accordance with the correction unit, based on, from out of the second image data, data including the first pixel whose pixel value has been replaced.

18. A non-transitory computer-readable storage medium storing a program for causing a computer to execute the method of controlling a radiation imaging apparatus, wherein
the radiation imaging apparatus comprises:
an image capturing unit including a plurality of pixels configured to convert incident radiation into electrical signals,
a storage unit configured to store position information of, from among the plurality of pixels, a first pixel which continuously outputs an abnormal pixel value;
a replacing unit configured to replace the pixel value of the first pixel with a preset setting value based on the position information;
a correction unit configured to detect, from among the plurality of pixels, a second pixel which is not stored in the storage unit and outputs an abnormal pixel value, and correct the pixel value of the second pixel,
the method comprises:
generating second image data by performing processing in accordance with the replacing unit on the first image data output from the image capturing unit; and
detecting and correcting the second pixel in accordance with the correction unit, based on, from out of the second image data, data including the first pixel whose pixel value has been replaced.

* * * * *